(12) United States Patent
El Bernoussi et al.

(10) Patent No.: US 10,562,073 B2
(45) Date of Patent: Feb. 18, 2020

(54) APPARATUS FOR MEASURING THE STIFFNESS OF MAILPIECES

(71) Applicant: Solystic, Bagneux (FR)

(72) Inventors: Hicham El Bernoussi, Paris (FR); Anthony La Paglia, Montelier (FR); Jean-Marc Teluob, Cornas (FR); Jean-Michel Reboul, Saint Donat (FR); Fabrice Eyraud, Portes les Valence (FR)

(73) Assignee: SOLYSTIC, Bagneux (FR)

( * ) Notice: Subject to any disclaimer, the term of this patent is extended or adjusted under 35 U.S.C. 154(b) by 0 days.

(21) Appl. No.: 15/575,592

(22) PCT Filed: May 17, 2017

(86) PCT No.: PCT/FR2017/051236
§ 371 (c)(1),
(2) Date: Nov. 20, 2017

(87) PCT Pub. No.: WO2018/011479
PCT Pub. Date: Jan. 18, 2018

(65) Prior Publication Data
US 2019/0168264 A1    Jun. 6, 2019

(30) Foreign Application Priority Data

Jul. 12, 2016   (FR) ..................................... 16 56684

(51) Int. Cl.
*G01N 3/20* (2006.01)
*B07C 1/16* (2006.01)

(52) U.S. Cl.
CPC ................. *B07C 1/16* (2013.01); *G01N 3/20* (2013.01); *B65H 2511/13* (2013.01); *B65H 2701/1916* (2013.01)

(58) Field of Classification Search
CPC ......... B07C 1/16; G01N 3/20; B65H 2511/13
(Continued)

(56) References Cited

U.S. PATENT DOCUMENTS 3,818,859 A * 6/1974 Kalmar ..................... A23B 7/16
                                                        118/24
6,032,517 A * 3/2000 Reisig ....................... B07C 1/16
                                                        73/37.7
(Continued)

FOREIGN PATENT DOCUMENTS

DE          1574165 A1   11/1971
WO   WO2004/030835 A1    4/2004
WO   WO-2004030835 A1 *  4/2004  ............... B07C 1/16

OTHER PUBLICATIONS

International Search Report for PCT/FR2017/051236, dated Jul. 19, 2017.

*Primary Examiner* — Terrell H Matthews
(74) *Attorney, Agent, or Firm* — Dickinson Wright PLLC (57) ABSTRACT

Apparatus for measuring the stiffness of mail articles on the principle of measuring deflection of a beam in bending comprises a rectilinear conveying portion for conveying the mail articles, a deflection roller disposed in a staggered offset manner between two wheels having deformable rims in such a manner as to form a substantially triangular peak on the rectilinear conveying portion, and an inlet ramp that is disposed upstream from the peak and that follows the upward slope of the peak.

19 Claims, 6 Drawing Sheets

(58) Field of Classification Search
USPC .......................................................... 209/600
See application file for complete search history.

(56) References Cited

U.S. PATENT DOCUMENTS

| | | | | |
|---|---|---|---|---|
| 6,386,537 | B1 * | 5/2002 | Howard | B65H 29/18 |
| | | | | 270/52.02 |
| 7,096,743 | B2 * | 8/2006 | Vogel | B07C 1/16 |
| | | | | 73/159 |
| 2004/0245158 | A1 * | 12/2004 | Redford | B07C 1/16 |
| | | | | 209/584 |
| 2005/0000299 | A1 * | 1/2005 | Vogel | B07C 1/16 |
| | | | | 73/849 |
| 2009/0013756 | A1 * | 1/2009 | Sanford | B07C 1/16 |
| | | | | 73/1.82 |
| 2019/0168264 | A1 * | 6/2019 | El Bernoussi | B07C 1/16 |

* cited by examiner

APPARATUS FOR MEASURING THE STIFFNESS OF MAILPIECES

CROSS-REFERENCE TO RELATED APPLICATIONS

This application is a national phase application under 35 U.S.C. § 371 of International Patent Application No. PCT/FR2017/051236, filed on May 19, 2017, which claims the benefit of French Patent Application No. 1656684, filed on Jul. 12, 2016, both of which are hereby incorporated by reference in their entireties.

TECHNICAL FIELD

The invention relates to measurement apparatus for measuring the stiffness of flat articles, and in particular of mail articles, which apparatus comprises a conveying portion along which the articles are conveyed in series and on edge, and a stiffness sensor operating on the principle of measuring deflection of a beam in bending, which sensor is disposed along said conveying portion for measuring in contactless manner the stiffness of each article.

The invention also relates to a postal sorting machine including such apparatus for measuring the stiffness of mail articles.

PRIOR ART

U.S. Pat. No. 6,032,517 discloses a postal sorting machine including measurement apparatus for measuring the stiffness of mail articles conveyed in series and on edge on a sorting conveyor.

In that apparatus, the stiffness measurement is taken in a curved portion of the sorting conveyor, which conveyor is a pinch belt conveyor.

That stiffness measurement apparatus operates on the principle of measuring the deflection of a beam in bending.

In particular, it comprises a first sensor disposed in a straight segment of the conveyor upstream from the curved portion for taking a first measurement that corresponds to a measurement of the thickness of the article, and a second sensor disposed in the curved portion of the conveyor for taking a second measurement that corresponds to a thickness measurement that takes into account the stretching of the belts of the conveyor that is caused by said article going along the curved portion.

The stiffest articles cause the belts to be stretched considerably in the curved portion while the most flexible articles do not cause the belts to stretch in the curved portion.

The difference between the two measurements, one upstream from the curved portion and the other in the curved portion, serves as a magnitude representative of the stiffness of the article that is passing through said curved portion.

That known measurement apparatus is not adapted for a wide range of mail articles going from a standard letter to large-format flat mail articles or "flats," such as catalogs or magazines having thick bindings.

If the radius of curvature in the curved portion of the conveyor is relatively small for reasons of compactness of the sorting installation, that can lead to deformation forces deforming the conveyor belts by stretching that are very large and that result in the mail articles being damaged under the effect of excessive force.

In addition, that measurement apparatus is not adapted for differentiating between mail articles having very high inherent stiffness such as a catalogue with a thick binding and mail articles having relative stiffness because they contain, for example, a very rigid object inside them, such as a pen or a metal plate such as a key. These are the articles that are the most likely to lead to jams in the conveyor of a postal sorting machine.

Document WO2004/030835 also discloses measurement apparatus for measuring the stiffness of flat mail articles. However, that apparatus does not make it possible to take measurements over a wide range of mail articles of non-uniform stiffness.

SUMMARY OF THE INVENTION

An object of the invention is thus to propose measurement apparatus that is adapted for measuring the stiffness of very non-uniform articles (such as mixed mail), going, for example from the conventional mailpiece to large-format flat mail articles such as catalogs and magazines and also mail articles having envelopes containing rigid objects inside them.

To this end, the invention provides measurement apparatus for measuring the stiffness of mail articles, which apparatus comprises a rectilinear conveying portion along which the articles are conveyed in series and on edge, and a stiffness sensor operating on the principle of measuring deflection of a beam in bending, which sensor is disposed along said conveying portion for measuring in contactless manner the stiffness of each article, a deflection roller being disposed in staggered offset manner between two wheels having deformable rims in such a manner as to form a substantially triangular peak on the conveying portion, said measurement apparatus being characterized in that an inlet ramp is disposed upstream from said peak relative to the conveying direction in which the flat articles are conveyed so as to cause the flat articles to follow the upward slope of the peak without any obstacle.

The basic idea of the invention is to cause the articles to be deflected to a small and controllable extent in a rectilinear conveying portion so as to take the stiffness measurement on the principle of measuring the deflection of a beam in bending.

With the ramp upstream from the peak, the articles are brought over a path tangential to the roller. The obstacle formed by the roller is thus removed from the rectilinear conveying path, thereby preventing articles from hitting said roller and causing large shocks.

The wheels having deformable rims are well adapted for transporting non-uniform articles having high variations in thickness at constant speed. This conveyor having wheels with deformable rims generates little vibration, thereby contributing to obtaining a stiffness measurement of good quality. Each wheel having a deformable rim may be a driving wheel, while the deflection roller may be an idler roller.

The measurement apparatus of the invention may advantageously have the following features:

an outlet ramp may be disposed downstream from said peak relative to the conveying direction of the articles, which ramp follows the downward slope of the peak, thereby making it possible to prevent the rear edge of a rigid article exiting from the peak from hitting the deflection roller and from disturbing the stiffness measurement;

the inlet ramp may extend upstream relative to the conveying direction beyond a pinch point between a wheel and said inlet ramp so as to form a disengagement zone for the rear ends of the articles, thereby enabling very stiff articles to position themselves without shocks and flat against the inlet ramp;

the upward slope of said inlet ramp may be less than or equal to 10°, which means that the deflection peak on the rectilinear conveying portion is small so as to preserve as far as possible the structural integrity of the articles conveyed on the conveyor of the measurement apparatus;

the sensor may advantageously be a multiple sensor suitable for performing multiple stiffness measurements at a plurality of points distributed over the height of the mailpiece on edge;

it may further comprise a data processor unit that, on the basis of multiple stiffness measurements respectively at the foot of the article and at the top of the article, evaluates whether the article is flexible enough or whether it is too stiff;

the evaluation may be based on a linear combination of deflection values; and the evaluation may be based on a statistical estimation of the deflection value on the basis of a reference database produced by off-line learning. The learning database is enriched dynamically during use.

The stiffness measurement apparatus may be installed in the rectilinear portion of a sorting conveyor of a postal sorting machine, preferably upstream from the conveyor in order to take a decision to sort the article arriving at the inlet of the conveyor if said article is flexible enough, or a decision to reject it if said article is too stiff, this decision being taken before the article is either directed to a sorting outlet or, conversely, directed to a reject outlet of the sorting conveyor.

BRIEF DESCRIPTION OF THE DRAWINGS

The present invention can be better understood and other advantages appear on reading the following detailed description of an embodiment given by way of non-limiting example and with reference to the accompanying drawings, in which.

DESCRIPTION OF EMBODIMENTS

Figure 1:
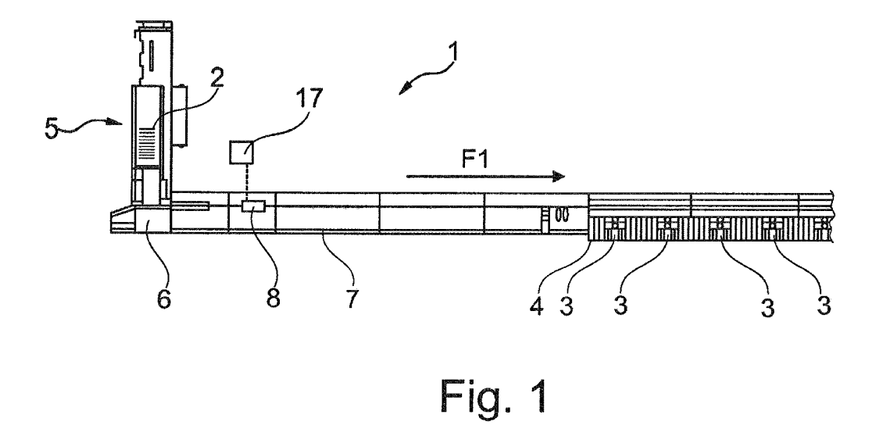
FIG. 1 is a highly diagrammatic view of a postal sorting machine seen from above and incorporating the stiffness measurement apparatus of the invention.

FIG. 1 is a fragmentary view of a postal sorting machine 1 designed to sort flat mail articles that are designated by reference 2 and that may be very non-uniform.

The mail articles may be very flexible, such as catalogues that are flexible but that have rigid edges, letters that are flexible but that contain rigid objects inside them (e.g. keys or pens), or indeed large-format flat articles of the type that are reinforced with cardboard or with some other rigid material, etc.

FIG. 1 shows sorting outlets 3, and a reject outlet 4 upstream from the sorting outlets 3.

The articles 2 are stacked on edge in the magazine 5 of an unstacker 6 that feeds the articles 2 in series and on edge into the sorting conveyor 7 that moves them towards the outlets 3 or 4 in a conveying direction indicated by arrow F1.

FIG. 1 also shows measurement apparatus 8 for measuring the stiffness of the articles 2.

As can be seen in FIG. 1, this measurement apparatus 8 is disposed in a rectilinear portion of the sorting conveyor 7 that, in this example, is upstream from the sorting outlets 3 and from the reject outlet 4. In this example, the measurement apparatus 8 is shown connected to a data processor unit 17 that, in this example, is also the monitoring and control unit for the sorting machine 1.

Figure 2:
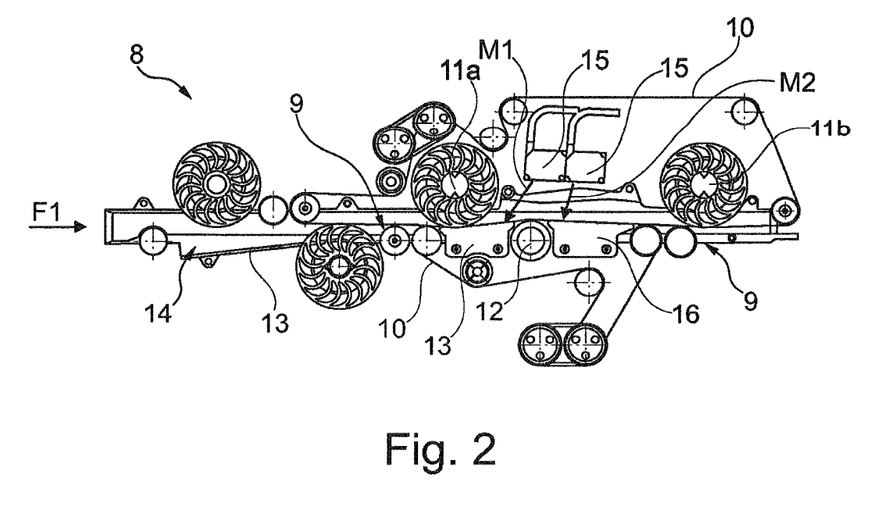
FIG. 2 is a more detailed diagrammatic view from above of the stiffness measurement apparatus of the invention.

As can be seen in more detail in FIG. 2, the measurement apparatus 8 of the invention has an essentially rectilinear conveying portion 9 that is formed by two parallel conveyor belts 10 that are adapted for moving the articles 2 on edge in the direction F1 by pinching them.

In this measurement apparatus of the invention, a deflection roller 12 over which one of the belts 10 is engaged is disposed in staggered offset manner between two wheels 11a and 11b having deformable rims and over which the other belt 10 is engaged in such a manner as to form a substantially triangular peak on the rectilinear conveying portion formed by the parallel belts 10.

In this example, each of the wheels has a hub provided with curved spokes for absorbing very non-uniform articles 2 of thickness that can range from less than one millimeter (mm) to a few centimeters (cm). In this example, the wheels 11a and 11b are wheels that are freely rotatably mounted and that are driven in rotation by a driving belt, and, in this example, the deflection roller 12 is a rigid idler roller for imparting the peak-shaped deflection to the articles.

The distance between the two wheels 11a, 11b having deformable rims is defined so that the largest of the articles 2 cannot be pinched by both wheels at the same time.

In accordance with the invention, an inlet ramp 13 is provided upstream from the peak formed by the roller 12 relative to the conveying direction in which the articles are conveyed, which ramp follows the upward slope of the peak that may be less than equal to 10°.

The inlet ramp 13 may be made of sheet metal or of a hard plastics material. It may extend upstream relative to the conveyor direction F1 beyond a pinch point between the wheel 11a and the inlet ramp 13 to form a disengagement zone 14 for the rear ends of the articles 2. In this way, even the articles that are very stiff arrive flat on the ramp 13 so that they are flat as they go over the peak of the rectilinear conveying portion.

FIG. 2 shows two sensors 15 on either side of the peak.

In particular, with a first sensor 15, a measurement indicated by arrow M1 is taken of the thickness of an article 2 pressed against the upward slope of the peak, while, with the other sensor 15, a second measurement indicated by arrow M2 is taken of the thickness of the article by taking into account the deformation of the belts 10 caused by the article 2 bending to go over the top of the peak. These two measures M1 and M2 are taken without coming into contact with the articles, and the difference between the two measurements is representative of the stiffness of the article.

The sensors 15 may be optoelectronic sensors such as laser sensors having depth gauges. As shown in FIG. 2, the sensors 15 are disposed outside the belts 10 and they measure depth relative to one of the two belts that is caused to be deformed as an article goes over the deflection peak. This depth measurement is equivalent to a thickness measurement upstream from the deflection peak.

An outlet ramp 16 may be disposed downstream from the peak relative to conveying direction F1, which outlet ramp follows the downward slope of the peak. FIG. 2 shows that the two ramps 13 and 16 have opposite slopes relative to the deflection roller 12.

Figure 3A:
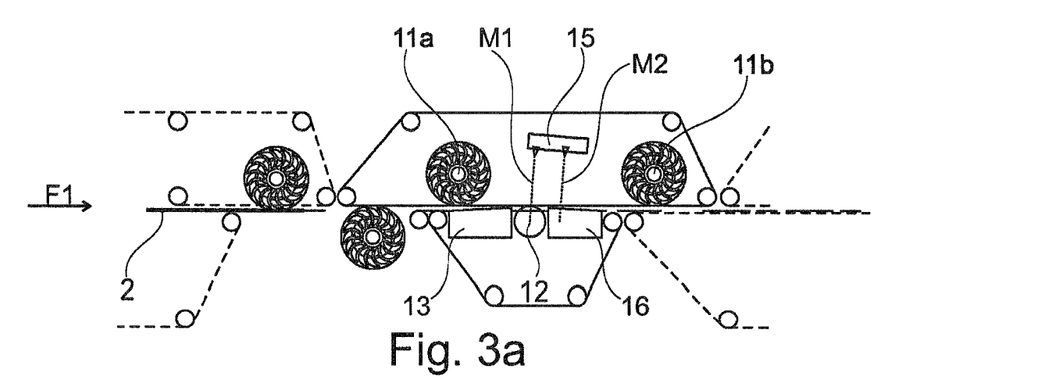
FIGS. 3a to 3e show the stiffness measurement apparatus of the invention at different stiffness measurement stages.

FIG. 3a shows a mail article 2 at the inlet of the stiffness measurement apparatus 8 of the invention.

Figure 3B:
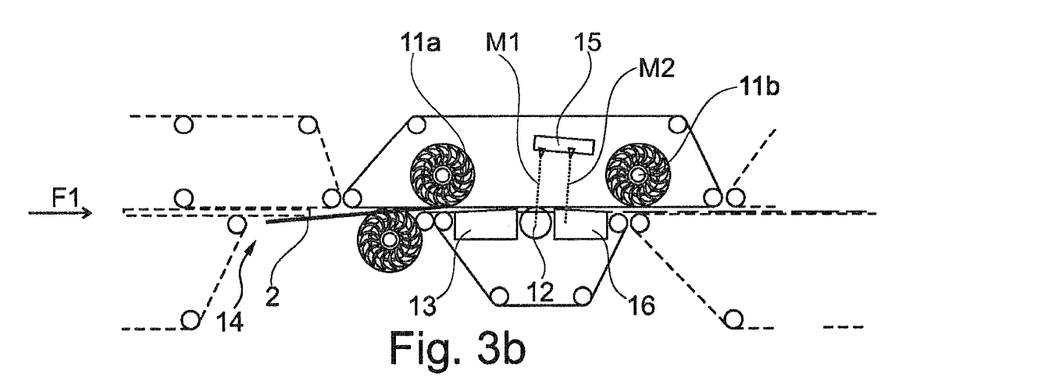

FIG. 3b shows the mail article 2 as pinched between the inlet ramp 13 and the deformable wheel 11a upstream from the roller 12. The rear end of the article 2 extends flat without bending in the disengagement zone 14.

Figure 3C:
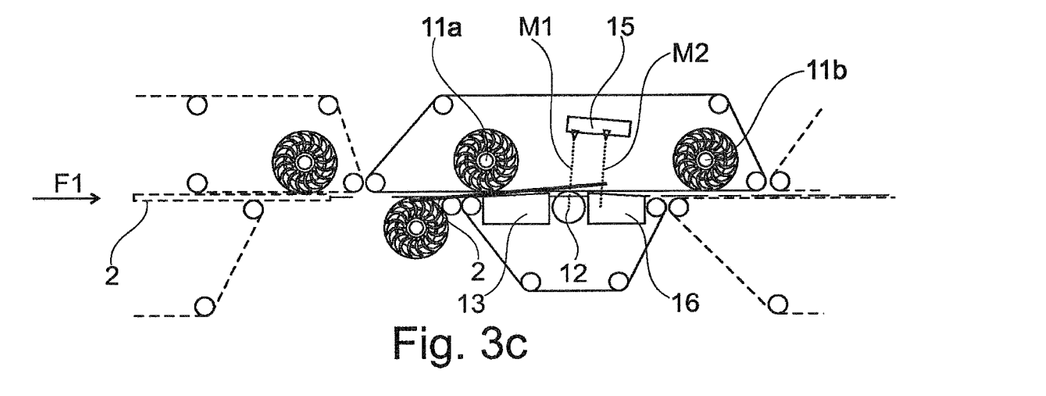

FIG. 3c shows the article 2 as it is bending to go over the roller 12 and with its rear end pinched between the wheel 11a and the ramp 13.

The sensors 15 take measurement samples over the article 2, while the article is advancing in the direction F1, so as to derive a stiffness profile as shown in FIGS. 4a to 4d.

Figure 3D:
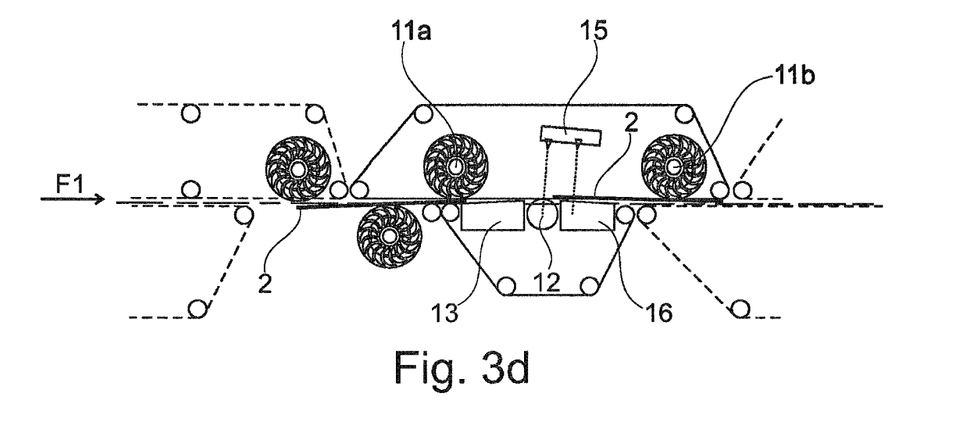

In FIG. 3d, the rear end of the current article 2 is finishing off going over the peak, and another article 2 is arriving at the inlet of the measurement apparatus.

Figure 3E:
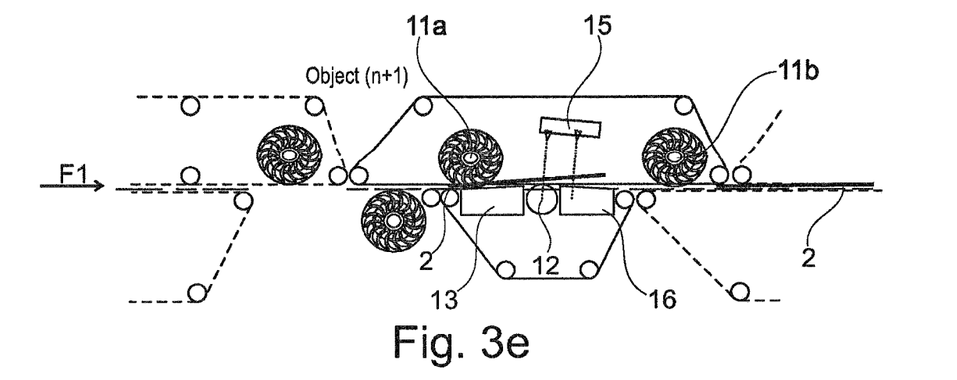

In FIG. 3e, the current article 2 is exiting from the measurement apparatus, while the front end of the other article 2 is bending to go over the peak.

In this example, the monitoring and control unit 17 is designed to establish a stiffness profile for each article 2.

Figure 4A:
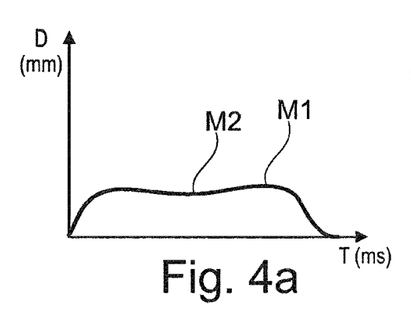
FIGS. 4a to 4d are graphs that show stiffness measurement signals for different types of article.

FIG. 4a shows a stiffness profile for a flexible and uniform mail article such as a letter. In this example, the stiffness profile is established in a frame of reference with a sampling time axis T and a thickness measurement axis D. In FIG. 4a, the sampled measurement signals M1, M2 obtained with the two sensors 15 are, in this example, coinciding plateau signals, and the measured thickness D does not vary upstream and downstream from the peak.

Figure 4B:
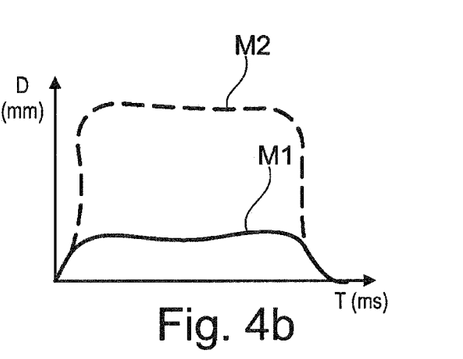

In FIG. 4b, the stiffness profile is that of a very rigid and uniform mail article such as a thick letter or a magazine. The measurement signal upstream from the peak M1 is different from the measurement signal M2 downstream from the peak. The two measurement signals are plateau signals and are spaced a long way apart from each other up the axis D.

Figure 4C:
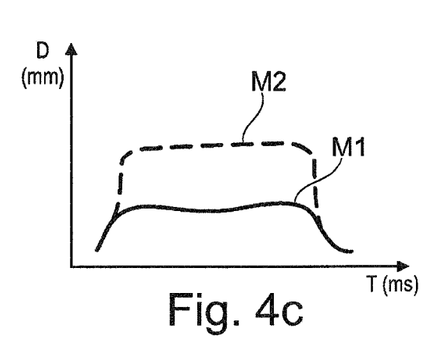

In FIG. 4c, the stiffness profile is that of a mail article of the type constituted by a flexible catalogue having a rigid edge. The measurement signals M1 and M2 are different and are similar to those shown in FIG. 4b, but they are spaced apart to a lesser extent up the axis D.

Figure 4D:
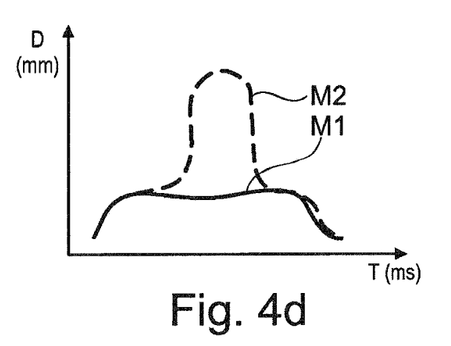

In FIG. 4d, the stiffness profile is specific to that of a flexible mailpiece containing a rigid object inside it, such as a key or a pen. The measurement signals M1 and M2 are different, the measurement signal M1 is a plateau signal, and the measurement signal M2 has a bell-shaped peak.

It can be seen that these stiffness profiles are quite distinctive from one another, and the unit 17 can be arranged so that, on the basis of the stiffness signals shown in FIGS. 4a to 4d, it detects whether a mail article can be directed towards a sorting outlet 3 (stiffness profiles of FIGS. 4a and 4d) or, conversely, should be directed towards the reject outlet 4 (stiffness profiles of FIGS. 4b and 4c).

This detection can be rendered finer by producing stiffness profiles at different heights over the articles 2.

Figure 5:
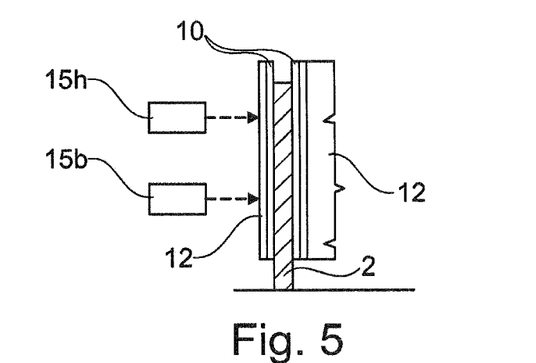
FIG. 5 shows a multiple sensor for performing multiple stiffness measurements over the heights of the articles.

FIG. 5 is a view in cross-section through an article 2 on edge that is pinched between the conveyor belts 10, and, in this example, with two superposed sensors 15h and 15b for taking thickness measurements respectively at the bottom of the article 2 on edge, e.g. 22 mm from the foot of the article, and at the top of the article 2, e.g. 60 mm from the foot of the article.

It is possible to provide more than two sensors, superposed at different levels over the height of the article 2 on edge.

With these multiple measurements, it is possible to identify better mail articles having envelopes containing rigid objects inside them, e.g. pens at the bottoms of the envelopes. It is known that that type stiff mail article tends to cause jams in automatic mail sorting machines and it is therefore important to be able to distinguish them from other mail articles without error.

A rigid object, made of metal or of some other material, and inserted in an envelope tends to be placed by gravity in the bottom of the envelope (in the vicinity of the foot of the mail item), and therefore the stiffness of the article is greater at the bottom of the mail item than at its top.

Figure 6A:
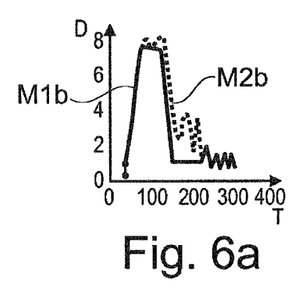
FIGS. 6a to 6h show multiple stiffness measurement signals for the measurements taken over the heights of the articles.
Figure 6B:
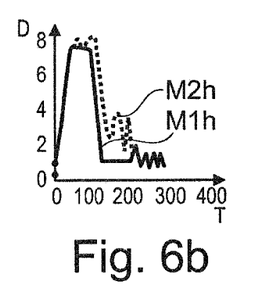

FIGS. 6a to 6d show different measurement signals produced at two levels over the height of a mail article having an envelope containing a rigid object such as a pen, e.g. at a height of 22 mm for the signals M1B and M2b, and at a height of 60 m for the signals M1h and M2h;

FIGS. 6a and 6b show the stiffness profile of a flexible mailpiece with thickness measurements taken at the bottom and at the top of the mailpiece.

Figure 6C:
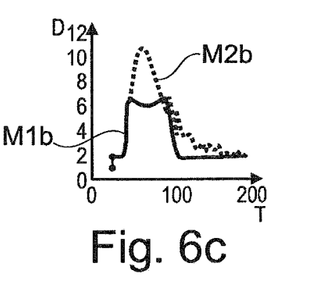
Figure 6D:
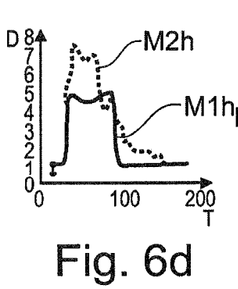

FIGS. 6c and 6d show the stiffness profile of a stiff mailpiece that can be directed towards a sorting outlet 3.

Figure 6E:
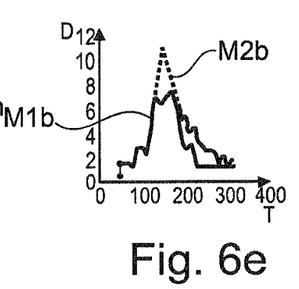
Figure 6F:
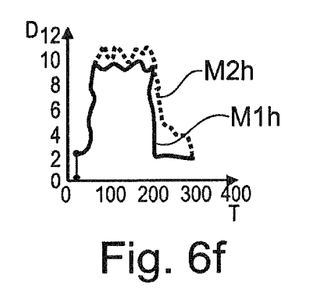

FIGS. 6e and 6f show the stiffness profile of a mail item having an envelope with a rigid object inside and that can be directed towards a sorting outlet 3 because the length of stiffness is short.

Figure 6G:
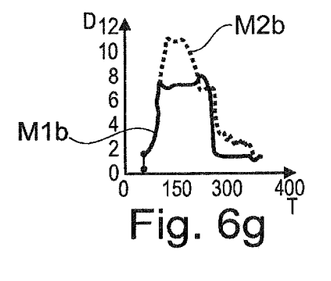
Figure 6H:
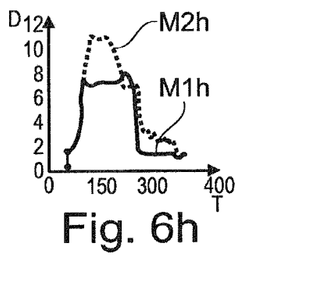

FIGS. 6g and 6h show the stiffness profile of a very stiff mailpiece with uniform stiffness over the entire height of the mailpiece, and also over the entire length of the mailpiece. This mailpiece is directed to the reject outlet 4.

Figure 7:
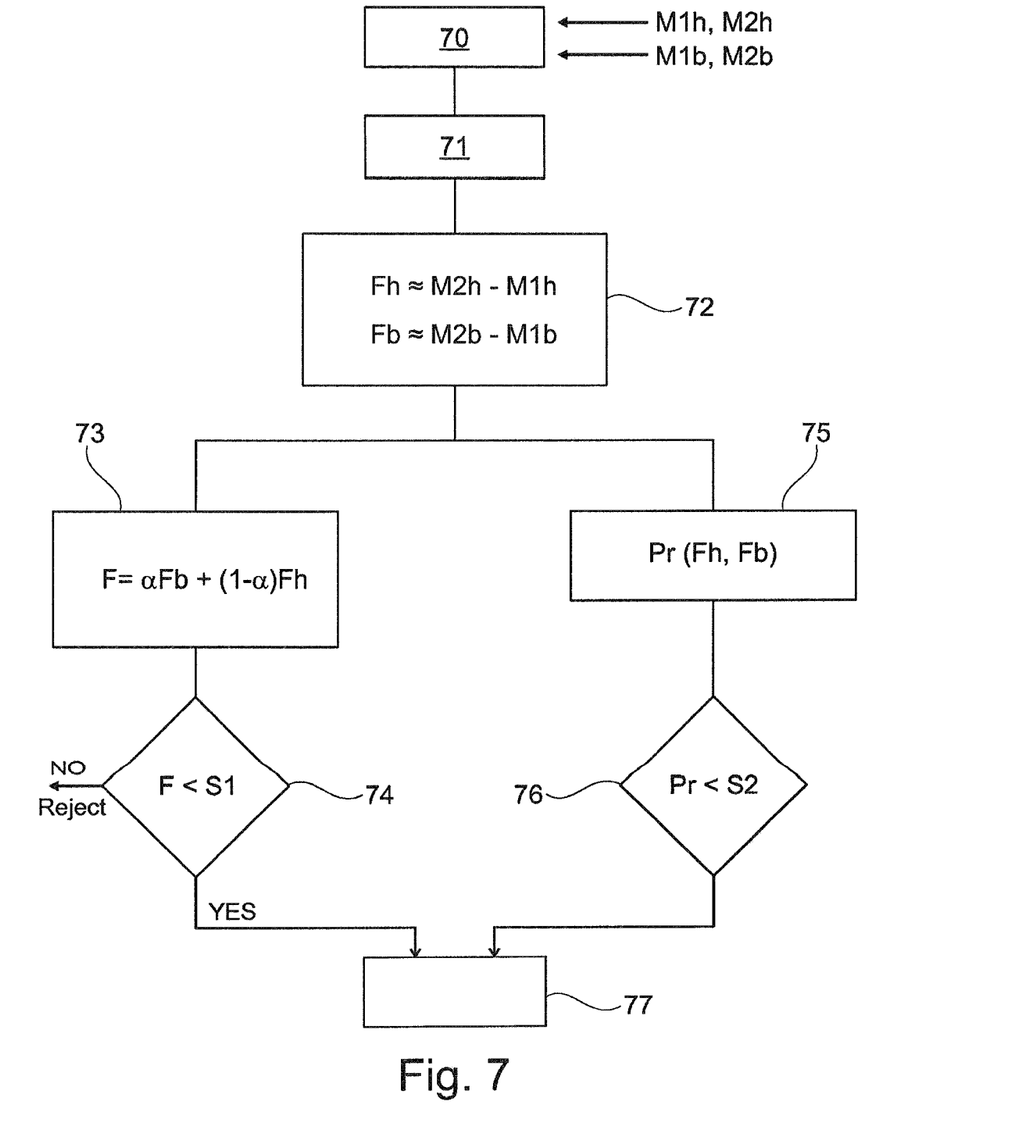
FIG. 7 is a block diagram showing the data processing performed for detecting articles that are too stiff.

FIG. 7 is a flow chart that shows a process for processing multiple signals for the stiffness profile M1h, M2h, M1b, M2b.

In step 70, the multiple stiffness profile signals M1b, M2b, M1h, M2h are sensed by sensors 15b and 15h upstream and downstream from the peak along the conveying portion in the measurement apparatus of the invention, and are delivered to the data processor unit 17.

In step 71, the unit 17 filters the signals so as to smooth them.

In step 72, the unit 17 computes the deflections (maximum deformation values) upwards and downwards for the article 2 using the following relationships:

$Fh = M2h - M1h$ $Fb = M2b - M1b$

In step 73, the unit 17 combines the two upward and downward deflection values for the article so as to derive a composite stiffness value F using the following relationship:

$F = \alpha Fb + (1-\alpha) Fh$ where the value of the coefficient α is chosen in such a manner as to express that high stiffness at the top of the article (in this example at a height of 60 mm) causes more jamming than high stiffness at the foot of the article.

In step 74, the stiffness value F is compared with an adjustable threshold S1 that can be adjusted as a function of the physical length and width characteristics of the articles that are to flow through the sorting machine, for example. If the value F is less than S1, the article may be considered as being flexible and the unit 17 directs said article to a sorting outlet 3. If the value F is greater than S1, the unit 17 directs the article 2 recognized as being too stiff towards the reject outlet 4.

By way of an alternative to step 73, the unit 17 performs step 75 in which it computes a statistical probability value Pr on the basis of the stiffness profiles Fh and Fb, which statistical probability value is representative of the probability that the article is a stiff mailpiece or a flexible mailpiece on the basis of the following relationships:

> Pr(Fh,Fb)=number of articles in a reference database that are recognized as being rigid with the stiffness profile (Fh,Fb)/total number of articles in the reference database with the stiffness profile (Fb,Fh).

The reference database is constructed in a prior learning phase of a neural network and it is advantageously increased dynamically by using the measurement apparatus.

In step 74, the unit 17 compares the probability value Pr with an adjustable threshold S2 that can be adjusted as a function of the physical length and width characteristics of the articles that are to flow through the sorting machine, for example.

If the value Pr is less than S2, the article can be considered as being too stiff and the unit 17 directs said article towards a reject outlet 4. If the value F is less than S1, the unit 17 directs the article 2 recognized as being flexible enough towards the sorting outlet 3.

The two stiffness assessments derived at 73 and 75 may be combined in step 77 so as to produce a decision that is even more precise in the unit 17 to direct the article towards a sorting outlet or to direct it towards the reject outlet.

In step 75, the statistical probability value may also be determined using a method based on logistic regression.

Naturally, the processing shown in FIG. 7 may be performed with more than two thickness measurements distributed over the height of an article 2.

For example, it is possible to take a first measurement at the bottom of the foot of the article on edge, a second measurement half way up, corresponding to the height at which the switching flaps for diverting articles into the sorting outlets are disposed, and a third measurement at a height even higher than the height at which the second measurement is taken. These multiple measurements make it possible to obtain stiffness profiles that are highly discriminating as a function of the types of the mail articles.

What is claimed is:

1. A measurement apparatus for measuring a stiffness of flat articles, comprising:
    a rectilinear conveying portion, wherein the flat articles are conveyed in series and on an edge;
    a stiffness sensor for measuring a deflection of a beam in bending, the stiffness sensor being disposed along the conveying portion for measuring in a contactless manner the stiffness of each flat article;
    a deflection roller being disposed in a staggered offset manner between a first wheel and a second wheel, the first and second wheels having deformable rims that form a substantially triangular peak on the conveying portion;
    disposed upstream from the peak relative to a conveying direction of the flat articles, wherein the flat articles follow an upward slope of the peak without any obstacle; and
    an inlet ramp, wherein an upward slope of the inlet ramp is less than or equal to 10°.

2. The measurement device of claim 1, further comprising an outlet ramp disposed downstream from the peak relative to the conveying direction of the flat articles, wherein the outlet ramp follows the downward slope of the peak.

3. The measurement apparatus of claim 1, wherein the inlet ramp extends upstream relative to the conveying direction beyond a pinch point between the first wheel and the inlet ramp to form a disengagement zone for rear ends of the flat articles.

4. The measurement apparatus of claim 1, wherein the stiffness sensor is a multiple sensor suitable for performing multiple stiffness measurements at a plurality of points distributed over a height of the flat articles.

5. The measurement apparatus of claim 4, further comprising a data processor unit, the data processor unit uses multiple stiffness measurements respectively at the foot of the flat article and at the top of the flat article to evaluate whether the flat article is flexible enough or too stiff.

6. The measurement apparatus of claim 5, wherein the evaluation is based on a linear combination of deflection values.

7. The measurement apparatus of claim 5, wherein the evaluation is based on a statistical estimation of a deflection value of a reference database produced by off-line learning.

8. The measurement apparatus of claim 7, wherein the reference database is increased dynamically during use.

9. The measurement apparatus of claim 1, further comprising:
    a postal sorting machine comprising:
        a sorting conveyor with sorting outlets; and
        a reject outlet; and
        wherein the conveying portion is upstream from the sorting outlets and from the reject outlet, and wherein the measurement apparatus is disposed at the conveying portion.

10. The measurement apparatus of claim 2, wherein the inlet ramp extends upstream relative to the conveying direction beyond a pinch point between the first wheel and the inlet ramp to form a disengagement zone for rear ends of the flat articles.

11. The measurement apparatus of claim 5, wherein the data processor unit uses the evaluation to direct the flat article towards a sorting outlet or a reject outlet disposed downstream of the conveying portion.

12. A postal sorting machine, comprising:
    a sorting conveyor with sorting outlets;
    a reject outlet;
    a conveying portion disposed upstream from the sorting outlets and from the reject outlet; and
    a measurement apparatus for measuring a stiffness of flat articles disposed at the conveying portion, the measurement apparatus, comprising:
        a rectilinear conveying portion, wherein the flat articles are conveyed in series and on an edge;
        a stiffness sensor for measuring a deflection of a beam in bending, the stiffness sensor is being disposed along said the conveying portion for measuring in a contactless manner the stiffness of each flat article;
        a deflection roller being disposed in a staggered offset manner between a first wheel and a second wheel, the first and second wheels having deformable rims that form a substantially triangular peak on the conveying portion; and
        an inlet ramp disposed upstream from said the peak relative to a conveying direction of the flat articles, wherein the flat articles to follow an upward slope of the peak without any obstacle.

13. The postal sorting machine of claim 12, further comprising an outlet ramp disposed downstream from the peak relative to the conveying direction of the flat articles wherein the outlet ramp follows the downward slope of the peak.

14. The postal sorting machine of claim 12, wherein the inlet ramp extends upstream relative to the conveying direction beyond a pinch point between the first wheel and the inlet ramp to form a disengagement zone for rear ends of the flat articles.

15. The postal sorting machine of claim 12, wherein an upward slope of the inlet ramp is less than or equal to 10°.

16. The postal sorting machine of claim 12, wherein the stiffness sensor is a multiple sensor suitable for performing multiple stiffness measurements at a plurality of points distributed over a height of the flat articles.

17. The postal sorting machine of claim 16, further comprising a data processor unit, the data processor unit uses multiple stiffness measurements at the foot of the flat article and at the top of the flat article to produce a stiffness assessment.

18. The postal sorting machine of claim 17, wherein the data processor unit uses the stiffness assessment to direct the flat article towards the sorting outlets or towards the reject outlet.

19. The postal sorting machine of claim 17, wherein the stiffness assessment is based on at least one of a linear combination of deflection values and on a statistical estimation of a deflection value of a reference database produced by off-line learning, wherein the reference database is increased dynamically during use.

* * * * *